(12) United States Patent
Kim (10) Patent No.: US 6,895,108 B2
(45) Date of Patent: May 17, 2005

(54) METHOD FOR INSPECTING DEFECTS IN THE SHAPE OF OBJECT

(75) Inventor: Myoung-jin Kim, Suwon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 367 days.

(21) Appl. No.: 10/147,048

(22) Filed: May 17, 2002

(65) Prior Publication Data

US 2002/0191833 A1 Dec. 19, 2002

Related U.S. Application Data

(63) Continuation of application No. 09/582,843, filed as application No. PCT/KR99/00663 on Nov. 5, 1999.

(30) Foreign Application Priority Data

Nov. 5, 1998 (KR) .............................. 98-47291

(51) Int. Cl.$^7$ ................................ G06K 9/00
(52) U.S. Cl. ................... 382/145; 348/129; 356/394; 250/559.39
(58) Field of Search ................ 382/145, 147, 382/148, 149, 151; 348/87, 94, 95, 126, 129, 130; 356/390, 394, 237.4, 237.5; 438/7, 16; 250/559.39, 559.45, 559.46; 702/40, 82, 172

(56) References Cited

U.S. PATENT DOCUMENTS

| | | |
|---|---|---|
| 4,484,081 A | 11/1984 | Cornyn .................. 250/559.46 |
| 5,305,392 A | 4/1994 | Longest ...................... 382/112 |
| 5,339,093 A | 8/1994 | Kumagai et al. ............. 345/89 |
| 5,550,933 A | 8/1996 | Stetten ....................... 382/199 |
| 6,087,673 A | 7/2000 | Shishido et al. ....... 250/559.45 |
| 6,091,845 A | 7/2000 | Pierrat et al. ............... 382/144 |
| 6,184,976 B1 | 2/2001 | Park et al. ............... 356/237.4 |

FOREIGN PATENT DOCUMENTS

| | | |
|---|---|---|
| CA | 2249265 | 10/1997 |
| DE | 3314465 A1 | 10/1984 |
| DE | 3347645 C1 | 10/1985 |
| EP | 0465233 A2 | 1/1992 |
| EP | WO 97/36260 | 3/1996 |

OTHER PUBLICATIONS

Canadian Office Action of the Canadian Patent Application No. 2,317,803 (dated Jan. 9, 2004).

Primary Examiner—Samir Ahmed
(74) Attorney, Agent, or Firm—Robert E. Bushnell, Esq.

(57) ABSTRACT

A method of inspecting for defects in the shape of an object, using an inspected image obtained from an object to be inspected, comprising the steps of: setting a reference image of a reference model for determining the defect in shape of the object to be inspected; obtaining the imaged image from the object to be inspected; comparing the corresponding whole or local area of the reference image with the inspected image in terms of brightness; and determining as to whether or not the object is defective in shape. According to the present invention, the shape defect inspection does not rely upon the skilled person's experience, can reduce time required for inspection, and can be made for the whole area of the inspection area.

20 Claims, 7 Drawing Sheets

FIG. 9A

METHOD FOR INSPECTING DEFECTS IN THE SHAPE OF OBJECT

CROSS-REFERENCE TO RELATED APPLICATIONS

This application is a continuation application of Applicant's Ser. No. 09/582,843 filed in the U.S. Patent & Trademark Office on the 5$^{th}$ day of Jul. 2000, and assigned to the assignee of the present invention.

CLAIM OF PRIORITY

This application makes reference to, incorporates the same herein, and claims all benefits accruing under 35 U.S.C. §119 from my application METHOD FOR INSPECTING DEFECTS IN THE SHAPE OF OBJECT filed with the Korean Industrial Property Office on the 5$^{th}$ day of Nov. 1998 and there duly assigned Ser. No. 47291/1998.

BACKGROUND OF THE INVENTION

1. Field of the Invention

The present invention relates in general to methods for inspecting for defects in the shape of such objects as chips, leads, and other constituent components employed in the processes for manufacturing semiconductors, and more particularly, to a method for inspecting defects in the shape of an object by comparing an image of an object to be inspected with a reference image of a reference model in terms of brightness.

2. Description of the Related Art

Conventionally, to inspect defects in the shape of objects such as chips and leads, and other constituent elements used in the production processes of semiconductors, a two-step inspection method has been widely used. The two steps are measurement and comparison.

According to the conventional method, a shape-defect inspection of the object has been carried out by an algorithm to inspect defects in the shape of the object through the two steps of measurement and comparison. Specifically, the conventional method is conducted as follows. First, an object to be inspected is physically measured to build data on the shape thereof, using a brightness distribution of an image. For example, a dimension of an external appearance of the object is physically measured in a linear dimension along a certain direction. Then, the measured data and the reference data of a reference model are compared with each other. As a result of the comparison, if the measured data is within a certain range, which is an allowable error for the reference data, the object is determined to be non-defective in shape. If not, the object is determined to be defective in shape.

References such as Park, U.S. Pat. No. 6,184,976 for APPARATUS AND METHOD FOR MEASURING AN AERIAL IMAGE USING TRANSMITTED LIGHT AND REFLECTED LIGHT, have endeavored to provide an aerial image measuring process to inspect various defects existing on patterns formed on a photo masks, while other references such as Pierrat et al., U.S. Pat. No. 6,091,845 for INSPECTION TECHNIQUE OF PHOTO MASK, contemplates providing an extended defect detection capability able to anticipate defects that would not otherwise be found until after the resist pattern is formed by using different mask elevations and interpolating the edges between masked and unmasked areas.

Shishido et al., U.S. Pat. No. 6,087,673 entitled METHOD OF INSPECTING PATTERN AND APPARATUS THEREOF, relies upon a determination of polarity of the difference image obtained from the comparison of specific pattern edges of two images. An allowable value for variation in the gradation value (that is, the value of light and shade) is either added or subtracted, so that the difference between the gradation values of the two images exerts no influence on the polarity of the difference image.

The conventional method using these steps of measurement and comparison is precise even with units of subpixel. These steps must be repeated however, for all elements representing the morphologic characteristics of the object to be inspected, thereby requiring a large amount of time in measurement and comparison.

To reduce the time of inspection, frequently some elements of the workpiece are only partially measured and compared. Selection of those elements to be precisely measured, and thus the integrity of the inspection and the ultimate determination of whether the object is defective in is shape or not is largely dependent upon the experience of skilled persons.

SUMMARY OF THE INVENTION

Accordingly, the present invention has been made keeping in mind the above problems occurring in the prior art, and an object of the present invention is to provide an improved process for reliably inspecting manufactured objects.

It is another object to provide a process for inspecting defects in the shape of objects without requiring the continuous presence of skilled technicians.

It is still another object to provide a process able to detect unacceptable defects observed in manufactured objects without requiring repetitious consideration of all of the morphologic characteristics of each manufactured object.

It is yet another object to provide a process able to detect and to determine whether deviations from a reference image are unacceptable defects in manufactured objects without requiring repetitious consideration of all of the morphologic characteristics of each manufactured object.

These and other objects of the present invention may be achieved with a process for inspecting for the presence of defects in the shapes of workpieces, by using an image obtained from the object. This process contemplates preparing a reference image derived from a reference model for the workpiece to be inspected, obtaining an image from each object to be inspected, making a comparison between a corresponding area of the reference image and the image obtained from the workpiece in terms of some optical characteristic of the image such as the brightness of either the area or of a feature of the workpiece that is within that area, and determining on the basis of the comparison whether or not the object is defective in shape.

Preferably, the comparison compares the brightness of a corresponding pixel from the image obtained with that of a pixel from the reference image. Substantively, the reference image provides a range of allowable errors in shape with a minimum value and a maximum value for each pixel.

In a particular implementation of the present invention, the reference image may be obtained by establishing an allowable brightness range for the pixel corresponding to an allowable range of positions for a border line of the object to be inspected, as a function of variation in brightness of the pixel relative to the position of the border line, and obtaining a minimum image and a maximum image from a minimum value and a maximum value in the allowable range of brightness for that pixel. Ideally, the function takes the existence of pixel noise into consideration.

A function that effectively makes a comparison of brightness is represented in the following expression:

$$C(Q;U,L)=\pi[l(i,j) \leq q(i,j) \leq u(i,j)], \qquad (1)$$

where: Q denotes the obtained image,

U denotes the maximum image and L denotes the minimum image,

C(Q;U,L) is a function of determining a defect in the shape of the image Q using the images U and L, l(i,j) denotes a brightness value of a pixel positioned on the coordinates (i,j) of the minimum image L, q(i,j) denotes a brightness value of a pixel positioned on the coordinates (i,j) of the image Q, and u(i,j) denotes a brightness value of a pixel positioned on the coordinates (i,j) of the maximum image U.

The image obtained from the workpiece and the reference image may be effectively represented in grayscale.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, in which like reference numerals indicate the same or similar components, and wherein.

DETAILED DESCRIPTION OF PREFERRED EMBODIMENTS

Hereinafter, the present invention will be described in more detail with respect to the accompanying drawings.

Figure 1:
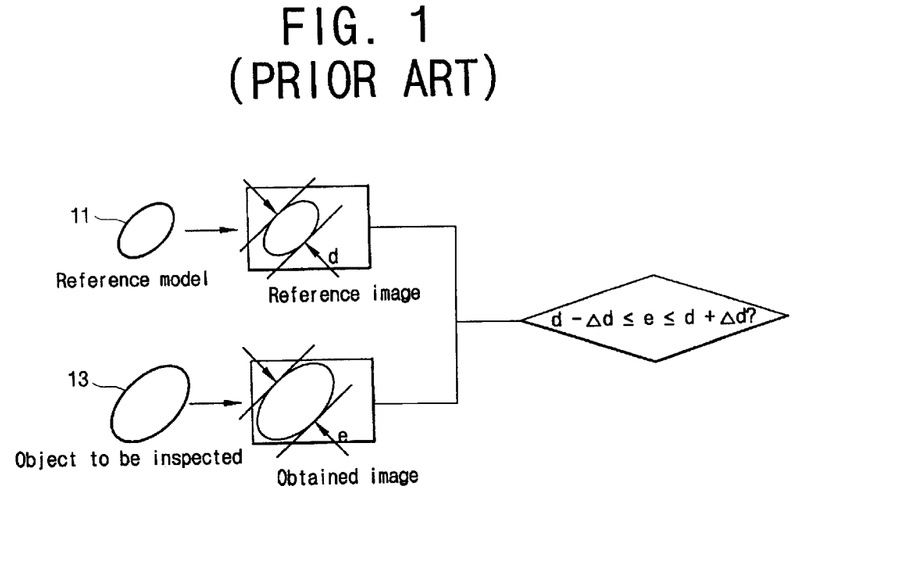
FIG. 1 is a schematic view illustrating a conventional method for inspecting for defects in the shape of an object.

FIG. 1 systematically shows a method of inspecting for the presence of defects in the shape of an object according to a conventional method wherein a shape-defect inspection of the object has been carried out by an algorithm to inspect defects in the shape of the object through successive steps of measurement and comparison. Referring to FIG. 1, an object 13 to be inspected is measured to obtain data about the shape of that object, on the basis of the distribution, using a brightness distribution of an image. For example, a dimension e of an external appearance of the object 13, a manufactured workpiece that has to be inspected, is measured along a certain direction. Then, the measured data such as the linear dimension e, and is the comparable reference data d for a reference model 11 are compared with each other. As a result of the comparison, if the measured data e is within the range of d±Δd, where Δd is an allowable error for the reference data d, the object 13 is determined to be non-defective in shape. If the value of e is not within that range however, the object 13 is determined to be defective in shape.

Figure 2:
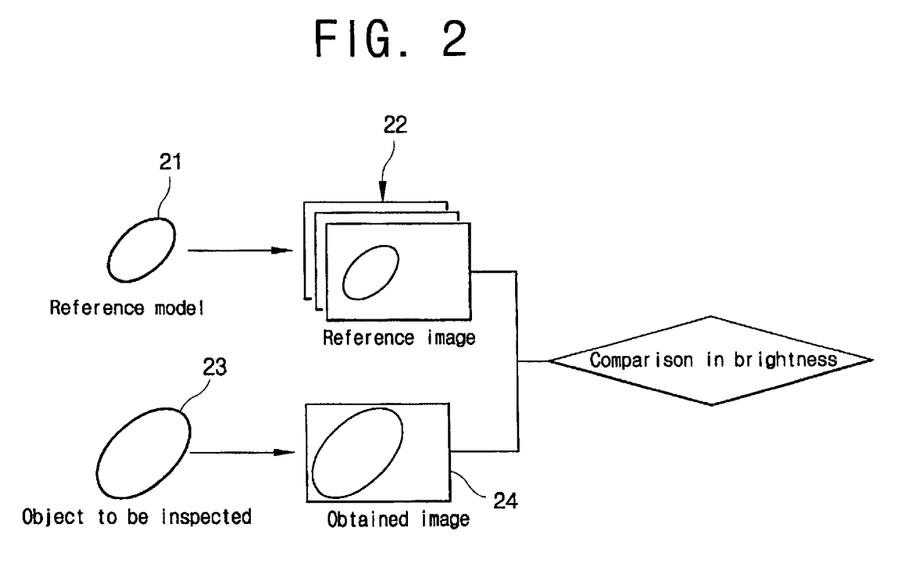
FIG. 2 is a schematic view illustrating a process as practiced according to the principles of the present invention for inspecting a workpiece for defects in its shape.

FIG. 2 is a schematic view showing a method for inspecting defects in the shape of an object according to the principles of the present invention. Referring to FIG. 2, reference images 22 are created to establish bases for making automatic visual inspections of objects such as manufactured workpieces in order to detect the presence of defects in the shapes of those objects. The reference images 22 are represented in grayscale relative to a reference model 21 for each the manufactured objects 23 to be inspected. Ideally, reference model 21 has accurate and precise dimensions for all of its discernable and morphologic features. In order to gauge an allowable range of errors in the shapes of workpieces 23, reference images 22 provide a maximum or first ideal image formed with pixels having a maximum value of brightness and a minimum or second ideal image formed with pixels having a minimum value of brightness within the range of the allowable error, as described in steps 104, 106 of FIG. 3. In essence, the plurality of reference images document the maximum and minimum values of brightness of each pixel of the areas that contain the features of the reference model that correspond to the features of the workpieces which should be inspected.

Then, an image 24 of an object to be inspected is obtained by using a camera (not shown) and the brightness value of each pixel of image 24 is compared with the stored brightness value of each corresponding pixel of reference images 22. If the brightness value of each pixel of image 24 is determined in steps 116, 118 to be between the brightness values of each corresponding pixel of reference images 22 defined by the minimum image and the maximum image, object 23 to be inspected is determined to be non-defective in shape. If the brightness value of any pixel of image 24 is determined in steps 116, 118 to be not between the brightness values of each corresponding pixel of reference images 22 however, object 23 may be determined to be defective in shape; usually, whether object 23 is sufficiently defective as to be beyond redemption is determined by either the total number or by the percentage of total pixels found to be outside of the range of tolerance.

Figure 3:
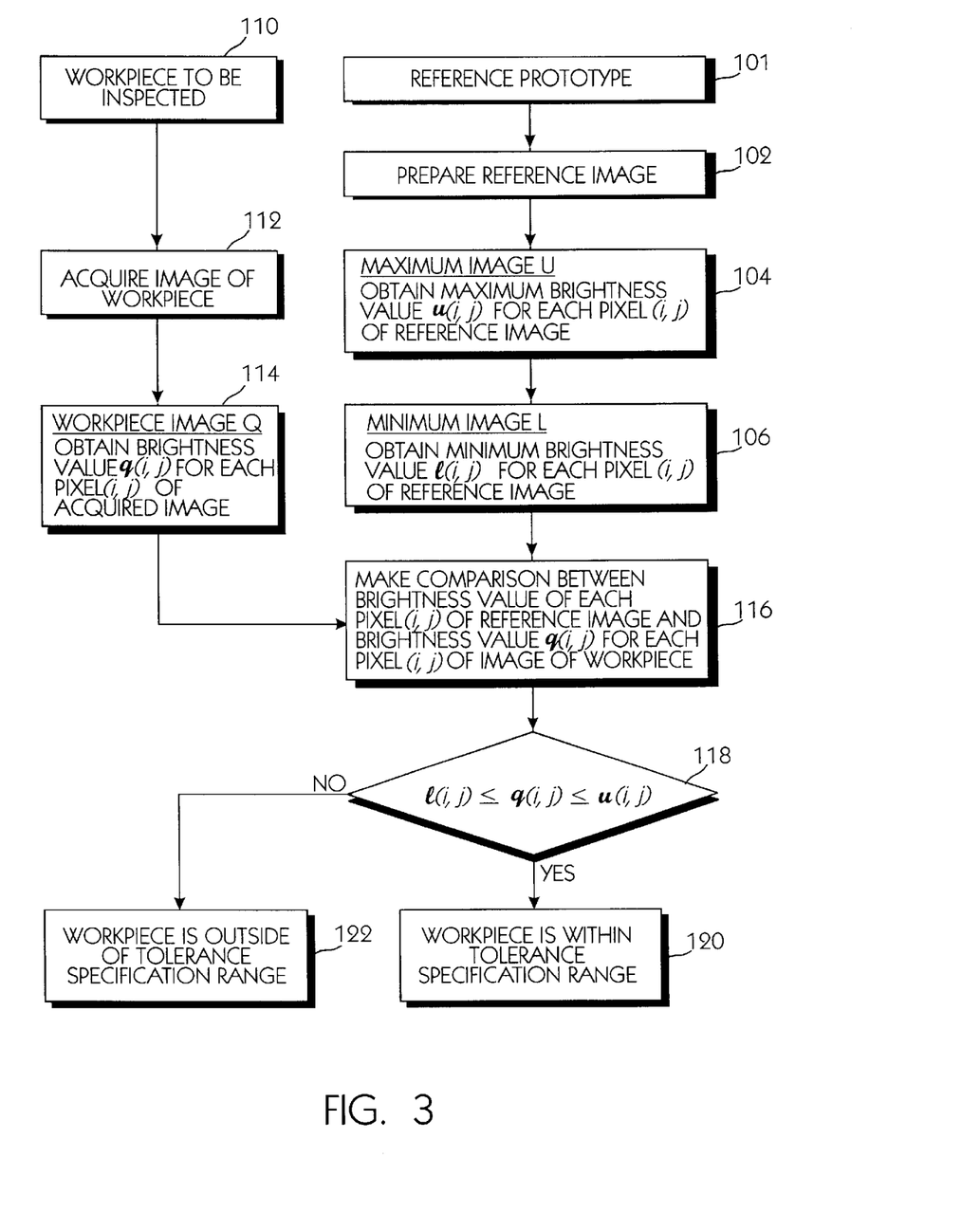
FIG. 3 is a flowchart empirically illustrating a series of steps for the practice of one embodiment of the present invention.

FIG. 3 empirically illustrates one possible arrangement of steps in the practice of a process of inspection conducted according to the principles of the present invention. In this process, a reference prototype 21 is prepared during step 101, and a reference image 22 of that prototype is prepared in step 102. The maximum brightness value u(i, j) is then determined in step 104 for each pixel (i,j) of the reference image, and during step 106, the minimum brightness value l(i,j) for each pixel (i,j) of the reference image is obtained.

Contemporaneously, the workpiece 23 to be inspected may be manufactured and an image of the workpiece acquired during step 110. Subsequently, during step 114, a brightness value q(i,j) may be obtained from image 24 for each pixel (i,j) of the acquired image obtained during step 112.

Subsequently, a comparison is made during step 116 between the brightness value of each pixel (i,j) of the reference image prepared during step 102, and the brightness value q(i,j) for each pixel (i,j) of the image of workpiece 23. If the brightness value q(i,j) is greater than or equal to the minimum brightness value l(i,j), but less than or equal to the maximum brightness value u(i,j), for each pixel obtained during step 114, the workpiece is determined to be within tolerance of the specification range in step 120. If the brightness value q(i,j) of any pixel of the acquired image obtained during step 114 is outside of that range however, that is, if the value q(i,j) for any pixel for a particular workpiece is less than the minimum brightness value l(i,j) or greater than the maximum brightness value u(i,j), then during step 122 the workpiece may be determined to be outside of the specified tolerance range.

The process described in the foregoing paragraphs will be described in more detail in the following paragraphs. First, the relation between positions on a border line of the object 23 to be inspected and the brightness values of pixels obtained from image 24 will be described in the following paragraphs.

Figure 4:
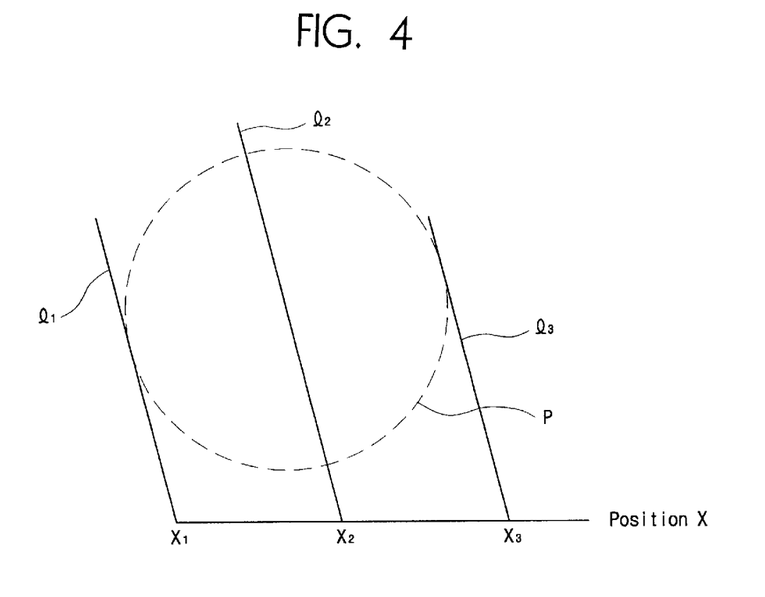
FIG. 4 is a graph showing a relation between positions of a border line defining an is external appearance of an object and a unit pixel of an image of the object.

FIG. 4 is a graph showing a relation between a sequence of possible positions of a border line that extends along a peripheral border defining an external appearance of one feature of object 23 and a unit pixel of image 24 acquired from object 23, and FIG. 4 is a graph showing the variation in brightness of the unit pixel of image 24 as a function of the sequence of possible positions of one morphological characteristic such as the right edge or perhaps a border line of object 23.

Referring to FIG. 4, a circle P indicated by dashed lines represents the unit pixel of image 24 obtained from the workpiece 23 being inspected, and oblique lines $l_1$, $l_2$ and $l_3$ represent a sequence of three of many possible different positions where a morphological feature such as the rightmost edge of workpiece 23 may be located. The linear separation between boundary lines $l_1$, $l_3$ is approximately equal to the diameter of unit pixel P, while the distance between boundary lines $l_1$, $l_2$ is approximately equal to the distance between $l_2$, $l_3$. That is to say, it is assumed for purposes of explanation that the location of the morphologic feature of object 23 to be inspected may be positioned at one of three oblique boundary lines $l_1$, $l_2$ and $l_3$, relative to the area of pixel P, so that the specific edge of workpiece 23 may be located during the inspection by reference to one of the sequence of oblique lines $l_1$, $l_2$ or $l_3$. Where the border line $l_1$ is either entirely to the left of or is tangential to pixel P, the position value of the border line $l_1$ is denoted as $X_1$. Where the border line $l_2$ passes through the center of the pixel P (i.e., where the edge of the feature being examined traverses pixel P), the position value of the border line $l_2$ is denoted as $X_2$. Where the border line $l_3$ is tangential to the diametrically opposite side of pixel P, still different features of workpiece 23 are included within pixel P, and the position value of the border line $l_3$ is denoted as $X_3$.

Figure 5:
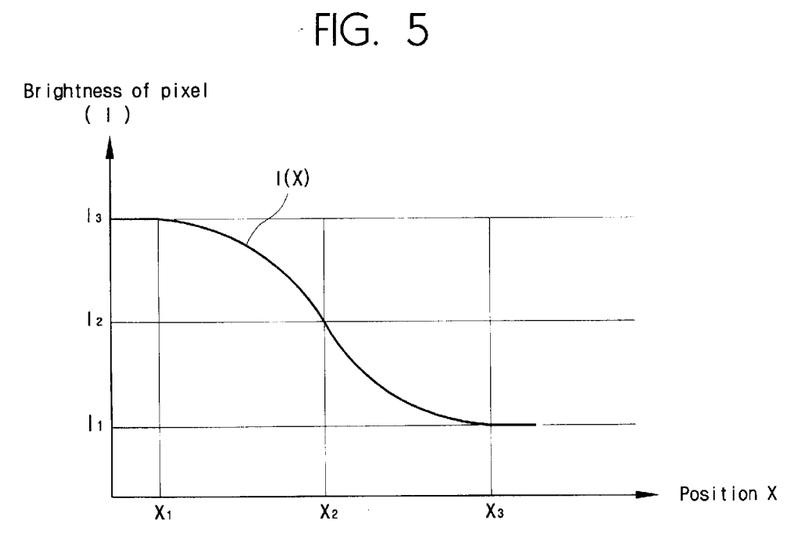
FIG. 5 is a graph showing variation in brightness of the unit pixel as a function of the positions of a border line of the object.

The brightness value I of pixel P varies as a function of the position value X, varies in magnitude between $I_3$ and $I_1$ as shown in FIG. 5. The brightness of each pixel varies as a function of the location of a morphologic feature such as a specific edge of object 23. Thus, if the brightness value I of pixel P is given, the position X on the border line of the object 23 can be estimated, such as by using the graph in FIG. 5. In other words, by using the brightness value I, a determination may be made from pixel P of whether workpiece 23 partially or completely coincides with the specification's range of tolerance. Alternatively, an algorithm may be employed to convert the result of the comparison between the brightness of the reference image 22 and the brightness of the image 24 into a gauge that indicates the displacement to the position of the edge of the feature of workpiece 23 from the position required by the specification.

Figure 6:
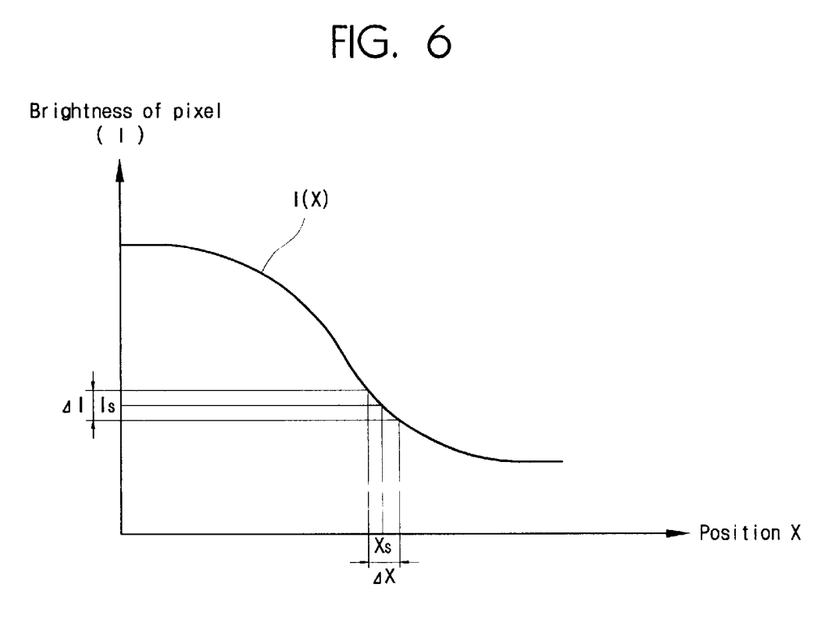
FIG. 6 is a two-coordinate graph illustrating the value of brightness corresponding to the positions of the border lines and the allowable brightness range corresponding to the allowable position range.

With respect to the allowable range of the images that are defined by the minimum image and the maximum image, the relation between an allowable position range $\Delta X$ and a corresponding allowable brightness range $\Delta I$ is as shown in FIG. 6.

After determining the position on the border lines X and the allowable position range $\Delta X$ for reference model 21, the value of brightness I corresponding to the position of the border lines X and the allowable brightness range $\Delta I$ corresponding to the allowable position range $\Delta X$, may be obtained by using the graph shown in FIG. 6. The minimum value and the maximum value of the allowable brightness range $\Delta I$ are utilized in forming the minimum image and the maximum image defining the allowable image range.

Subsequently, a determination is made of whether the brightness value of each air corresponding pixel of the image 24 is within the allowable brightness range $\Delta I$. If the brightness value of each corresponding pixel obtained from image 24 is within the allowable brightness range $\Delta I$, the object is determined to be non-defective in shape. If not, object 23 is determined to be defective in shape. For comparison, the pixels to be compared may be selected from among a pixel P aligned relative to border line $l_1$, a pixel P traversed by border line $l_2$, and a pixel P aligned relative to border line $l_3$ as depicted in FIG. 4.

Figure 8:
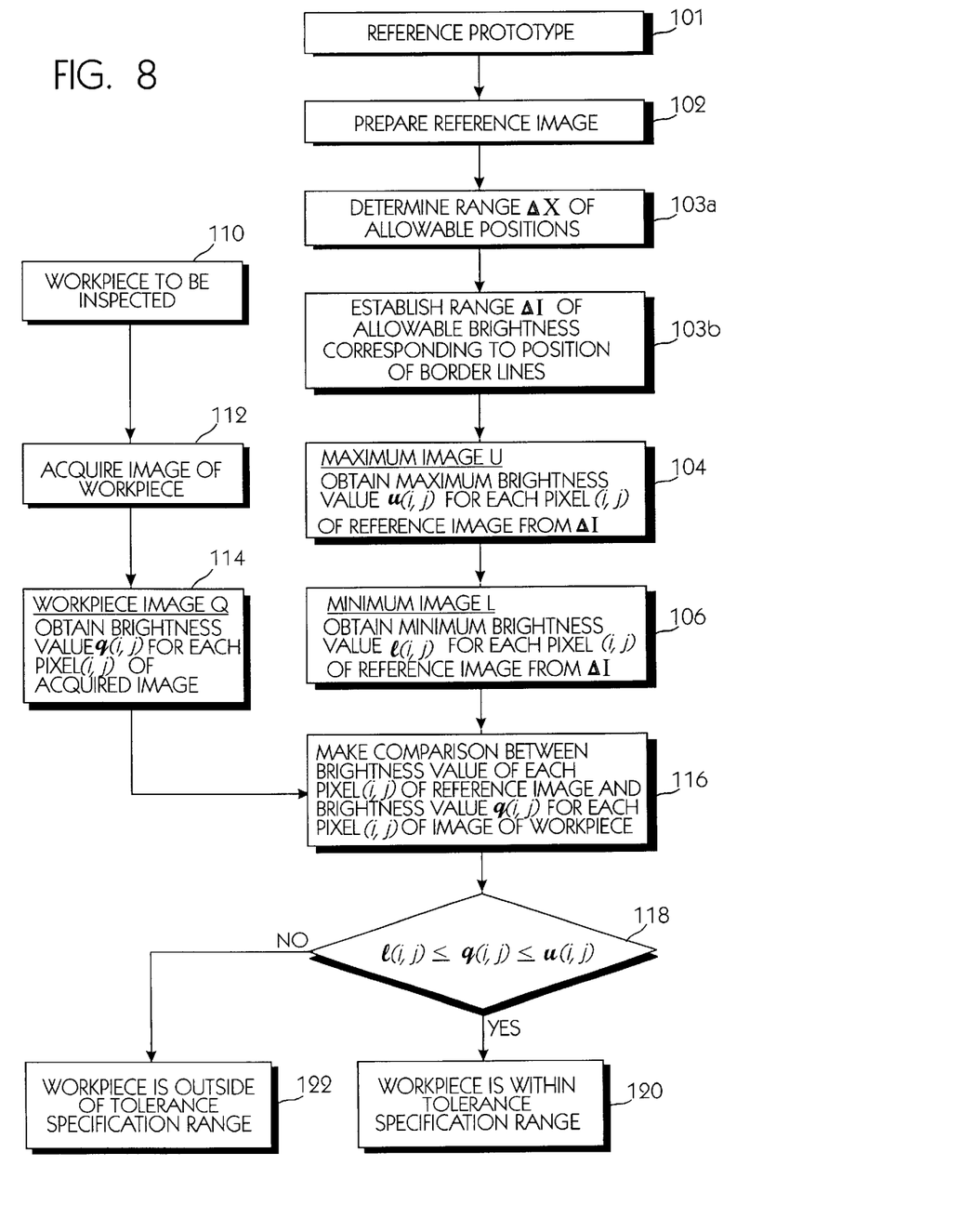
FIG. 8 is a flow chart illustrating one embodiment using brightness to detect manufacturing errors.

Turning now to the flow chart illustrated in FIG. 8, a determination is made in step 103a of the range $\Delta X$ of allowable positions of the boundary lines, and subsequently, in step 103b, the range $\Delta I$ of allowable brightness is established to correspond to the positions of those border lines, as is illustrated in FIG. 6. Subsequently, in steps 104, 106 the maximum brightness value and minimum brightness values are obtained, and the comparison is made in step 116.

Figure 7:
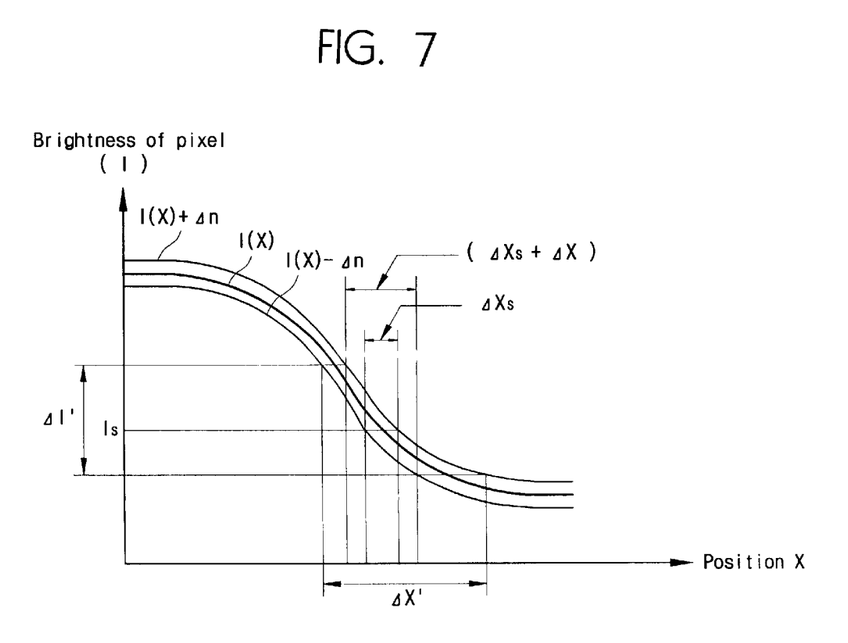
FIG. 7 is a two-coordinate graph illustrating the relations between the range for allowable brightness and the range of actually determinable boundary positions.

If pixel noise occurs in the reference image while conducting a sequence of this inspection process, an error in the result of the inspection may incorrectly indicate a defect in the shape. FIG. 7 is a graph showing the process for obtaining an allowable brightness range $\Delta I'$ when pixel noise is present. FIG. 7 demonstrates that the amplitude of pixel noise, $\pm\Delta n$, influences the determination of the brightness of the pixel I(X).

Where pixel noise within an amplitude range of $\pm\Delta n$, exists, a position of the border line of the reference model 21 corresponding to the brightness Is is given a range of $\Delta Xs$ as shown in FIG. 7. Considering the allowable position error $\Delta X$, the range of allowable position errors for the border lines is $\Delta Xs+\Delta X$ and the corresponding range for the allowable brightness is $\Delta I'$.

Corresponding to the range for the allowable brightness $\Delta I'$, the range for the actually determinable position is extended to $\Delta X'$. That is, the range for a determinable position $\Delta X'$ due to the presence of pixel noise $\pm\Delta n$ is increased to beyond the allowable position error range $\Delta Xs+\Delta X$. The less the pixel noise is, the closer the determinable range $\Delta X'$ is to $\Delta Xs$:

$$\text{Lim}\Delta X' = \Delta X \qquad (2)$$

where $\Delta n \rightarrow 0$

Figure 9:
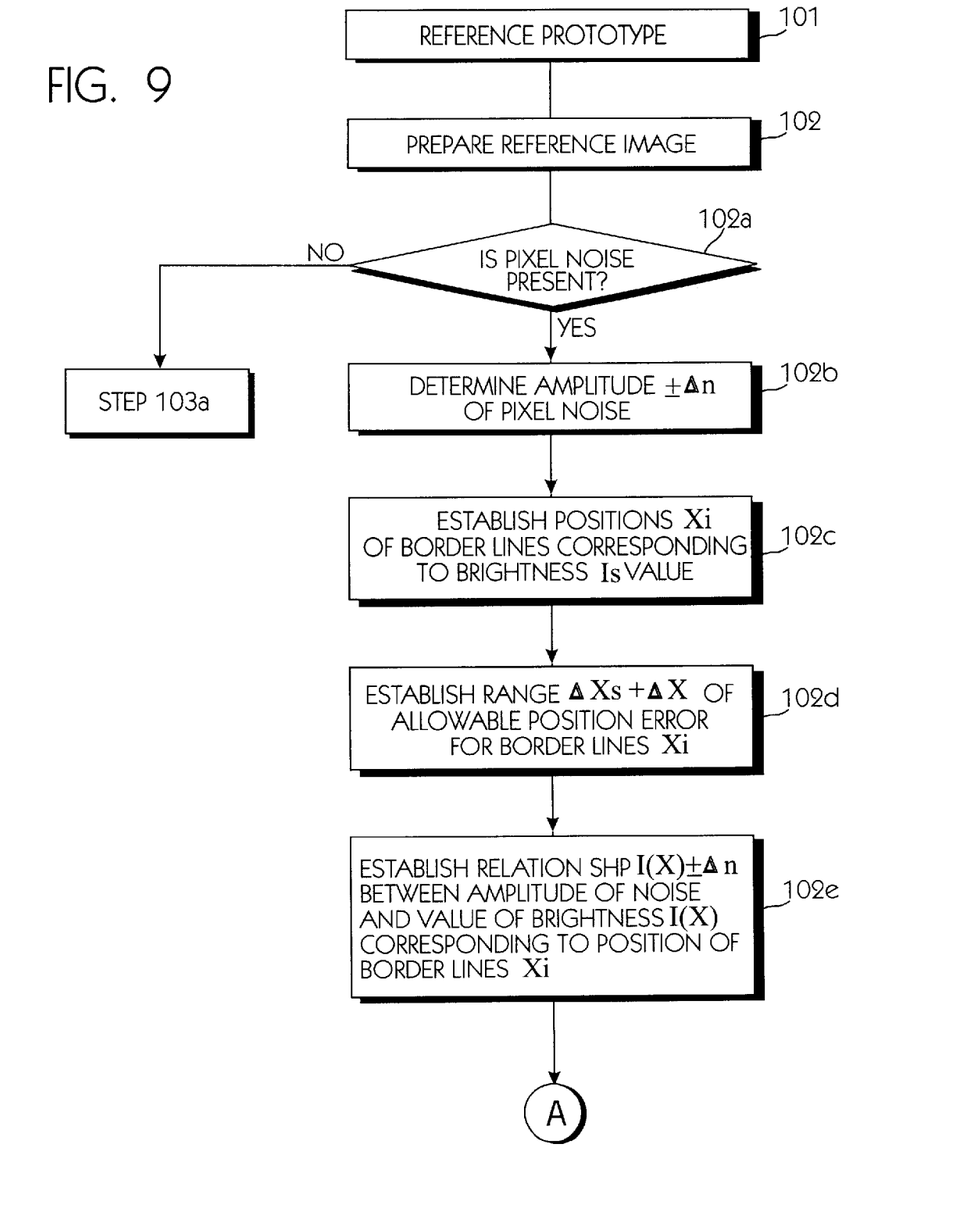
FIGS. 9 and 9A are flowcharts illustrating other embodiment to compensate for the presence of noise when using brightness to detect the occurrence of manufacturing errors.
Figure 9A:
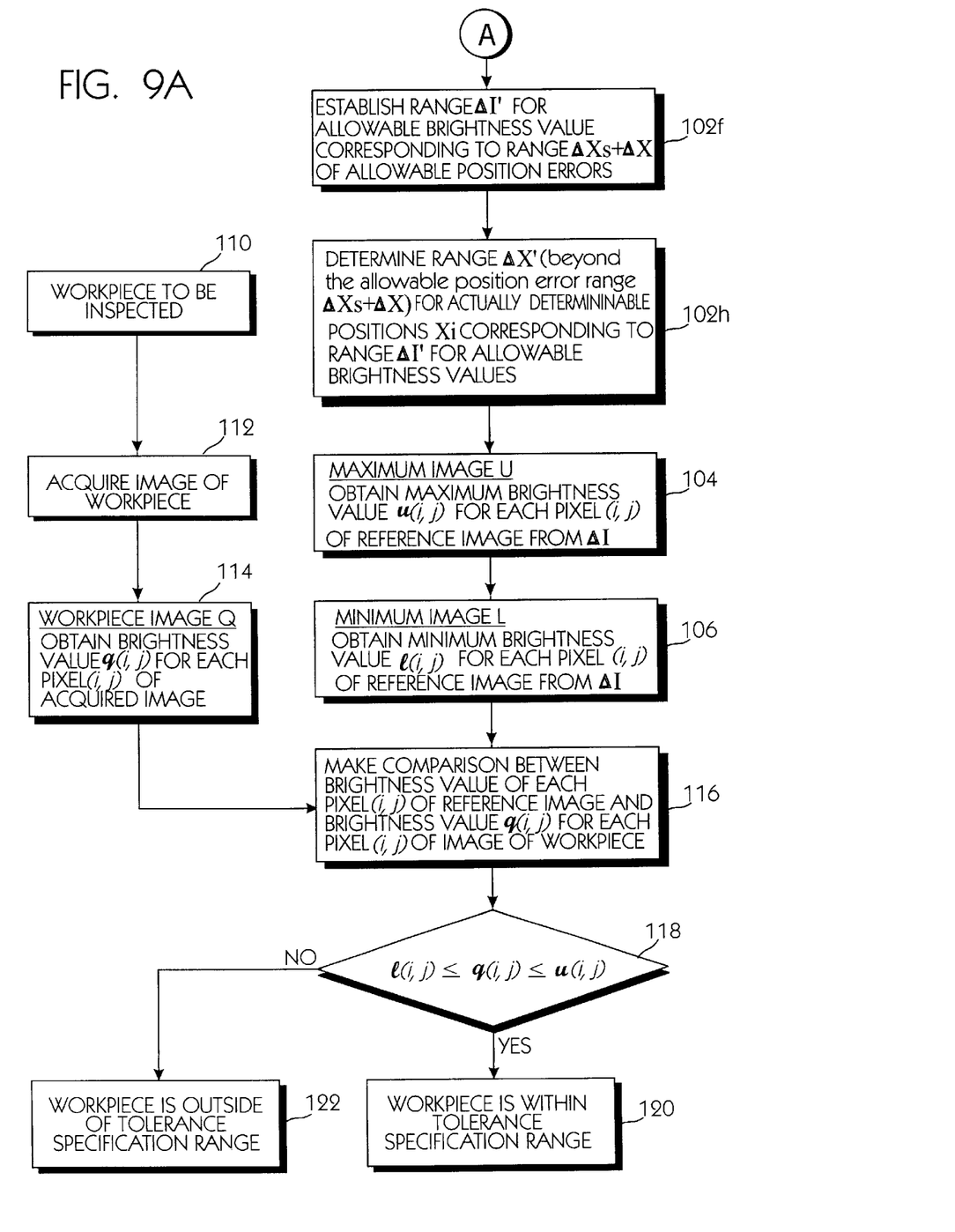

Referring now to FIGS. 9 and 9A in conjunction with the graph of FIG. 7, a determination is made in step 102a where the pixel noise is present. If no pixel noise is perceived, step 103a as illustrated in FIG. 8 is undertaken, followed by step 103b and subsequently by the comparison in step 116 and the determination in step 118. If pixel noise is present however, the amplitude $\pm\Delta n$ of the pixel noise is determined in step 102b and the positions $X_i$ of border lines corresponding to the brightness value Is is established in step 102c. A range $\Delta Xs+\Delta X$ of allowable position errors for the border lines $X_i$ is established in step 102d while a relationship $I(X)\pm\Delta n$ between the amplitude of the pixel noise and the value of the brightness $I(X)$ corresponding to the positions of the border lines $X_i$ is established in step 102e. In step 102f, the range $\Delta I'$ for allowable brightness values is established to correspond to the range $\Delta Xs+\Delta X$ of the allowable position errors for the boundary lines, and in step 102g the range $\Delta X'$ (beyond the allowable position error range $\Delta Xs+\Delta X$ is established for the actually determinable positions $X_i$ corresponding to the range $\Delta I'$ for the allowable brightness values. Subsequently the maximum and minimum brightness values are obtained in steps 104, 106 a comparison is made in step 116 and the determination of acceptability, or non acceptability is made in step 118.

If the image 24 is denoted Q, the allowable maximum image is denoted U, and the allowable minimum image is denoted L, the function $C(Q; U,L)$ for determining the shape-defect of an object can be expressed as follows:

$$C(Q;U,L) = \pi[l(i,j) \leq q(i,j) \leq u(i,j)], \qquad (3)$$

where: $l(i,j)$ is a brightness value of a pixel positioned on the coordinates $(i,j)$ of the minimum image L, $q(i,j)$ is a brightness value of a pixel positioned on the coordinates $(i,j)$ of the image Q, and $u(i,j)$ is a brightness value of a pixel positioned on the coordinates $(i,j)$ of the maximum image U.

If the brightness values of all the pixels included in the inspection area are within the allowable brightness range defined by the minimum image and the maximum image, the object to be inspected is determined to be non-defective in shape. If not, the object is determined to be defective in shape.

The inspection area that is formed by the gathered pixels whose brightness values are used for the brightness comparison, is included in the image of the object to be inspected, and may be the entire area or only a local area of the image as necessary to complete the inspection of the workpiece.

The criteria for final determination as to whether the object is defective in shape or not may be established differently if necessary, according to the kind of the object to be inspected. An arbitrary threshold number, such as 80% of the pixel included in the inspected area, may be chosen. For example, if over 80% of the pixels included in the inspected area have their brightness values within the allowable brightness range, the object to be inspected is determined to be non-defective in shape. If not, the object to be inspected is determined to be defective in shape.

The following table (Table 1) shows a result of an experiment by a conventional shape defect inspection method that relies upon measurement of dimensions and comparison, and a shape defect inspection method using a brightness comparison according to the principles of the present invention when an object to be inspected is a lead frame with a random shape.

TABLE 1

Result of experiment by conventional method and present method

| Inspection method | Conventional method | Present Method |
|---|---|---|
| Measure time | 6 msec/object | 0.4 µsec/object |
| Inspected area | Local area | Entire area |
| Others Distinctions | Position for measurement: depends upon the skilled worker's experience | Various applications are available, inspection for foreign matters and contamination is available |

As seen from the Table 1, according to the conventional method, one measurement takes 6 µsec/object whereas it takes 0.4 µsec/time according to the present method. Thus, where the whole image of a workpiece is formed by 300,000 pixels that represent the lead frame when that frame is the object to be inspected, the time required for measuring twenty areas on that frame is, at maximum is about 120 milliseconds according to the present invention, whereas it is about 1,800 sec (30 minutes) according to the conventional method. In summary, the conventional method requires a longer period of time for inspection and limits the inspection area to the object's local area, but it is unavailable for an inspection of the whole area. Unlike this, the time required for inspection is short and the inspection area can be extended to the entire area of the workpiece according to the present method. The present invention is also effective in enhancing the precision of inspection without requiring continuous reliance upon the presence of a skilled technician.

As described above, an object's shape-defect inspection method according to the present invention is conducted by grayscale comparison of each corresponding pixel. Therefore, the shape-defect inspection does not rely upon a skilled technician's experience, can reduce time required for inspection, and can be conducted for the entire surface area of the object to be inspected.

An object's shape-defect inspection performed according to the present invention can accommodate an allowable error on the order of units of subpixels, and may readily be applied to the process for manufacturing semiconductors requiring for high-speed and high-precision.

Although the present invention has been described in connection with a preferred embodiment thereof, it will be appreciated by those skilled in the art that additions, modifications, substitutions and deletions not specifically described may be made without departing from the spirit and scope of the invention as defined in the appended claims.

What is claimed is:

1. A method of inspecting for defects in an object, comprising the steps of:

preparing a reference image representing at least a portion of a shape as a grayscale of unidirectionally varying unique values extending across a boundary of the shape within a range of tolerance accommodating occurrence of pixel noise;

obtaining an image from the object to be inspected;

making a comparison between an optical characteristic of corresponding areas of said reference image and the image obtained from the object; and making a determination of whether said optical characteristic for said image obtained is within said range of tolerance of said corresponding area of said reference image.

2. The method of claim 1, with said comparison comprising a step of comparing brightness of a reference pixel of said image obtained with a corresponding pixel of said reference image.

3. The method of claim 1, further comprised of deriving from said reference image a minimum image and a maximum image that accommodate allowable errors in shape of the object by defining said range of tolerance.

4. The method of claim 3, further comprised of obtaining said reference image by:
   obtaining an allowable brightness range of said reference pixel corresponding to an allowable position range of a border line of the object to be inspected, based on a function of variation in brightness of said reference pixel relative to the position of the border line; and
   obtaining said minimum image and said maximum image respectively from a minimum value and a maximum value in the allowable range of brightness of said reference pixel.

5. The method according to claim 4, wherein the function considers an existence of a pixel noise.

6. The method according to claim 4, wherein an operation for the brightness comparison is represented in the following expression:

$$C(Q;U,L)=\pi[l(i,j)\leq q(i,j)\leq u(i,j)],$$

where:
   $l(i,j)$ is a brightness value of a pixel positioned on the coordinates $(i,j)$ of the minimum image L,
   $q(i,j)$ is a brightness value of a pixel positioned on the coordinates $(i,j)$ of the image Q, and
   $u(i,j)$ is a brightness value of a pixel positioned on the coordinates $(i,j)$ of the maximum image U.

7. The method according to claim 1, further comprised of representing said image obtained and said reference image in grayscale.

8. The method of claim 1, further comprised of:
   deriving from said reference image a minimum image and a maximum image for each of said corresponding areas of said reference image; and
   establishing said range of tolerance in dependence upon said minimum image and said maximum image.

9. A method of inspecting for defects in an object, comprising the steps of:
   preparing a reference image representing at least a portion of a shape as a grayscale of unidirectionally varying unique values extending across a salient feature of the shape within a range of tolerance accommodating occurrence of pixel noise;
   establishing a minimum value and a maximum value of a characteristic common to each of a plurality of reference pixels forming said reference image;
   obtaining an image from the object to be inspected;
   making a comparison between a representative value of said characteristic for each of a plurality of inspection pixels forming said image obtained from the object, and said minimum value and said maximum value for a corresponding one of said reference pixels;
   making a determination of whether the object to be inspected is within a range of manufacturing tolerance, in dependence upon said comparison.

10. The method of claim 9, further comprised of:
   establishing said minimum value and said maximum value to gauge deviations between said salient feature and corresponding feature of the object;
   using said minimum value and said maximum value to set said range of tolerance; and
   rejecting the object whenever said determination establishes that a plurality of said representative values are outside said range of tolerance.

11. The method of claim 9, further comprised of:
   setting a minimum value in correspondence with a minimum degree of brightness provided by said reference image; and
   setting said maximum value in correspondence with a maximum degree of brightness provided by said reference image.

12. The method of claim 9, further comprised of:
   deriving from said reference image a minimum image and a maximum image for each of said corresponding areas of said reference image; and
   establishing said range of tolerance in dependence upon said minimum image and said maximum image.

13. The method of claim 9, further comprised of compensating for a presence of said pixel noise in said reference image by adjusting said minimum value and said maximum value.

14. The method of claim 9, further comprised of using brightness of said reference pixels and brightness of said inspection pixels as said optical characteristic.

15. The method of claim 9, further comprised of making said comparison in accordance with the following expression:

$$C(Q;U,L)=\pi[l(i,j)\leq q(i,J)\leq u(i,j)],$$

where:
   $(i,j)$ is a brightness value of a pixel positioned on the coordinates $(i,j)$ of a minimum image L provided by said reference image,
   $q(i,j)$ is a brightness value of a pixel positioned on the coordinates $(i,j)$ of the image Q provided by said inspection image, and
   $u(i,j)$ is a brightness value of a pixel positioned on the coordinates $(i,j)$ of the maximum image U provided by said reference image.

16. The method of claim 10, further comprised of making said comparison in accordance with the following expression:

$$C(Q;U,L)=\pi[l(i,j)\leq q(i,j)\leq u(i,J)],$$

where:
   $l(i,j)$ is a brightness value of a pixel positioned on the coordinates $(i,j)$ of a minimum image L provided by said reference image,
   $q(i,j)$ is a brightness value of a pixel positioned on the coordinates $(i,j)$ of the image Q provided by said inspection image, and
   $u(i,j)$ is a brightness value of a pixel positioned on the coordinates $(i,j)$ of the maximum image U provided by said reference image.

17. The method of claim 11, further comprised of making said comparison in accordance with the following expression:

$$C(Q;U,L)=\pi[l(i,j)\leq q(i,j)\leq u(i,J)],$$

where:

l(i,j) is said minimum degree of brightness obtained from a pixel positioned on the coordinates (i,j) of a minimum image L provided by said reference image, q(i,j) is a brightness value of a pixel positioned on the coordinates (i,j) of the image Q provided by said inspection image, and u(i,j) is said minimum degree of brightness obtained from a pixel positioned on the coordinates (i,j) of the maximum image U provided by said reference image.

18. A method of inspecting for defects in an object, comprising the steps of:

preparing a reference image representing at least a portion of a shape as a grayscale of values varying unidirectionally across a distinctive feature of the shape, between a minimum value and a maximum value of the grayscale;

establishing from said reference image, a range of tolerance accommodating occurrence of pixel noise between said minimum value and said maximum value;

obtaining an image from the object;

making a comparison in portions where the reference image and the inspection image mutually correspond, between a representation of said distinctive feature for each of a plurality of inspection pixels forming said image, and said range of tolerance; and making a determination of whether the object meets manufacturing specifications, in dependence upon said comparison.

19. The method of claim 18, further comprised of establishing said minimum value and said maximum value to gauge deviations between said salient features and corresponding features of the object;

using said minimum value and said maximum value to set said range of tolerance; and rejecting the object whenever said determination establishes that a plurality of said representative values are outside said range of tolerance.

20. The method of claim 18, further comprised of making said comparison in accordance with the following expression:

$$C(Q;U,L)=\pi[l(i,j)\leq q(i,j)\leq u(i,j)],$$

where:

l(i,j) is a brightness value of a pixel positioned on the coordinates (i,j) of a minimum image L provided by said reference image, q(i,j) is a brightness value of a pixel positioned on the coordinates (i,j) of the image Q provided by said inspection image, and u(i,j) is a brightness value of a pixel positioned on the coordinates (i,j) of the maximum image U provided by said reference image.

* * * * *